United States Patent
Selland

(10) Patent No.: US 6,507,748 B2
(45) Date of Patent: Jan. 14, 2003

(54) COMPRESSION APPARATUS FOR DIAGNOSTICALLY EXAMINING BREAST TISSUE

(75) Inventor: Donna-Lee Selland, Needham, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 146 days.

(21) Appl. No.: 09/749,604

(22) Filed: Dec. 28, 2000

(65) Prior Publication Data

US 2001/0053880 A1 Dec. 20, 2001

Related U.S. Application Data

(60) Provisional application No. 60/173,744, filed on Dec. 30, 1999.

(51) Int. Cl.[7] ................................................. A61B 5/05
(52) U.S. Cl. ........................... 600/407; 378/37; 378/208
(58) Field of Search .......................... 600/407; 378/37, 378/208; 128/915

(56) References Cited

U.S. PATENT DOCUMENTS

| | | | |
|---|---|---|---|
| 3,578,971 A | 5/1971 | Lasky | 250/50 |
| 3,971,950 A | 7/1976 | Evans et al. | 250/451 |
| 3,973,126 A | 8/1976 | Redington et al. | 250/444 |
| 4,090,084 A | 5/1978 | Epstein et al. | 250/439 R |
| 4,259,585 A | 3/1981 | Novak et al. | 250/456 |
| 4,691,333 A | 9/1987 | Gabriele et al. | 378/37 |
| 4,943,986 A | 7/1990 | Barbarisi | 378/37 |
| 4,962,515 A | 10/1990 | Kopans | 378/37 |
| 5,595,177 A * | 1/1997 | Mena et al. | 128/653.1 |
| 5,855,554 A * | 1/1999 | Schneider et al. | 600/407 |
| 6,122,542 A * | 9/2000 | Lee et al. | 600/427 |
| 6,304,770 B1 * | 10/2001 | Lee et al. | 600/427 |

FOREIGN PATENT DOCUMENTS

| | | | |
|---|---|---|---|
| EP | 0 002 244 | 6/1979 | A61B/6/00 |
| EP | 0 288 187 | 10/1988 | A61B/6/00 |
| EP | 0 543 801 | 5/1993 | A61B/6/00 |

* cited by examiner

*Primary Examiner*—John Fox
(74) *Attorney, Agent, or Firm*—Michael A. Sanzo; Fitch, Even, Tabin & Flannery

(57) ABSTRACT

The present invention is directed to an apparatus that can be used for compressing breast tissue during diagnostic procedures. The apparatus maintains a flat rigid surface against breast tissue during imaging but contains a removable element that allows access to the breast for performing a biopsy without repositioning the breast.

10 Claims, 6 Drawing Sheets

COMPRESSION APPARATUS FOR DIAGNOSTICALLY EXAMINING BREAST TISSUE

CROSS REFERENCE TO RELATED APPLICATIONS

The present application claims the benefit of U.S. provisional application No. 60/173,744, filed on Dec. 30, 1999.

FIELD OF THE INVENTION

The present invention is directed to an apparatus for compressing breast tissue during diagnostic procedures and which contains an element that may be removed to permit access to the breast for biopsy. In addition, the invention encompasses improved diagnostic procedures that make use of this apparatus.

BACKGROUND OF THE INVENTION

During routine mammographic procedures, breast tissue is compressed in order to obtain higher quality images. Typically, a flat, rigid surface is used to maintain uniform pressure on the breast (see e.g., U.S. Pat. Nos. 4,090,084; 3,578,971; and 3,973,126), but devices having curved surfaces or rounded ridges have also been used (see e.g., U.S. Pat. Nos. 3,971,950; 4,962,515). If an abnormality appears on a mammogram, a needle biopsy is often performed to determine whether the lesion observed is cancerous.

Needle biopsies of breast tissue normally take place in two stages. In the first part of the procedure, an imaging technique is performed in order to accurately target the abnormality. Breast tissue is again compressed to improve resolution, but the device used must permit subsequent access to the breast for needle insertion. Thus, compression devices typically have either an opening or a section with perforations (see, e.g., U.S. Pat. No. 4,691,333). Unfortunately, both of these types of devices have undesirable features. Devices with an opening or "window" create an uneven pressure during imaging and poorer resolution pictures. Devices with perforations may also cause uneven pressure (albeit to a lesser degree) and may limit access to the breast. Ideally, a compression device should generate uniform pressure for imaging but subsequently allow access to the breast for needle placement while maintaining tissue in an immobilized state.

SUMMARY OF THE INVENTION

In its first aspect, the present invention is directed to an apparatus that can be used for compressing breast tissue during a diagnostic imaging technique or needle biopsy. The apparatus has two distinct plates. There is a planar bottom plate containing a smaller open region, or "window," that can be localized over the breast. In addition, there is a planar top plate that is designed to fit over and make substantially even contact with the bottom plate. The top plate has a raised element that corresponds to and fits inside the window of the bottom plate. This raised element should be of a thickness such that when the two plates make contact, the window in the bottom plate is filled to form an essentially flat lower surface for contacting breast tissue. Thus, the raised element should be elevated to the thickness of the bottom plate. For example, if the bottom plate were 3 mm thick, the raised element should be elevated approximately 3 mm above the plane of the top plate. The insertion of the raised element into the opening of the bottom plate should not result in a gap of greater than about 0.2 cm on any one side. For example, if the opening in the bottom plate were 4 cm by 8 cm, the raised region element of the top plate should typically have dimensions of about 3.9 cm by 7.9 cm.

In addition, the apparatus contains means for holding the top and bottom plates together with sufficient force to prevent the plates from separating when the apparatus is used diagnostically to compress breast tissue, i.e., the lower surface of the bottom plate should remain substantially flat during the diagnostic procedure. In most cases, the opening in the bottom plate will have a grid along its edges to aid in needle placement during biopsy. For example, one edge of the opening may contain a series of numbers while a second edge running perpendicular to the first has a series of letters.

The particular means for holding plates together is not critical to the invention. Screws may be inserted or the two plates may simply be held in place with clamps. In one design, the bottom plate has a substantially perpendicular end piece along at least two opposing ends that the top plate will fit between. These end pieces may have holes for the insertion of screws that also enter corresponding holes in the top plate and hold it in place. Alternatively, the top plate may have substantially perpendicular end pieces with holes for screws. These holes are aligned with corresponding holes in an endwall running along the sides of, and perpendicular to, the bottom plate. Screws are inserted through the two sets of holes to hold the plates together. In addition, the anterior edge of the top plate is slid under a reinforcing piece attached to the anterior endwall of the bottom plate to prevent the upward displacement of the top plate during breast compression procedures.

In a second aspect, the invention is directed to an improved method for compressing breast tissue during needle biopsy by applying pressure using an apparatus with a removable member. The removable member fills an opening in the apparatus to form a flat surface for contacting breast tissue. It is then removed, without repositioning the breast, to form an open region for needle placement during biopsy. Preferably, the apparatus will correspond to one described above.

The invention also encompasses an improved method for diagnostically examining breast tissue for a cancerous lesion. The method entails performing an imaging procedure in which breast tissue is compressed with an apparatus having a flat, planar lower surface with a removable member in contact with the breast undergoing examination. The removable member is then withdrawn without moving the breast in order to form an opening for performing a needle biopsy. Again, it is preferred that an apparatus as described above be used in the method.

BRIEF DESCRIPTION OF THE FIGURES

FIG. 1 is a front view showing one design of a breast compression apparatus. The bottom plate contains an opening and is attached to a support arm to allow it to be positioned against the breast undergoing examination. The top plate contains a raised element that fits inside the opening in the lower plate. In the device depicted, the bottom plate has two substantially perpendicular, opposing end pieces with screw holes. These are matched by similar holes in the top plate and allow the apparatus to be held together with screws during a diagnostic procedure.

FIG. 2 is a front cutaway view of the two plates of FIG. 1 after they have been brought together. The plates are held in place with one screw at either end and the raised element in the top plate has been inserted into the opening of the bottom plate to form a flat lower surface for contacting the breast.

FIG. 3 is a front cutaway view of a top compression plate having an alternative design to that shown in FIG. 1. In this design, the top plate, rather than the bottom, has opposing perpendicular end pieces with holes for screws. The screws are shown inserted in the end pieces and, after the top plate is joined with the bottom, they are inserted into corresponding holes in the bottom plate. The raised element of the top plate is shown as reference numeral (14). The portion of the raised element that lies above the main plane of the compression plate (marked with asterisks in the figure) fits snugly within the open region of the bottom compression plate to form a flat lower surface in contact with the breast. Recessed from the raised element is a reinforcing wall (16) that is perpendicular to the plane of the plate.

FIG. 4 is a drawing of the top compression plate of FIG. 3, viewed from above. The posterior portion of the plate has a permanently attached reinforcing portion (16). The raised element of the plate (14) lies at the anterior edge of the plate, i.e. the edge that would be against the chest wall of a subject during breast imaging.

FIG. 5 is a top view of a bottom plate (1) for a compression apparatus. The smaller, internal rectangular region (3) is open and contains a grid along each edge (15). The plate is shown joined to two attachments for support arms (2). A reinforcing piece (17) is attached to the anterior endwall that is perpendicular to the plane of the bottom plate. This piece extends slightly out over the plane of the bottom plate and is raised sufficiently above the plate to form a lip under which the anterior edge of the top plate may be slid. During imaging, the reinforcing piece of the lower plate helps to keep the anterior edge of the upper plate from lifting.

FIG. 6 is a representation of the top and bottom compression plates of FIGS. 3–5. The smaller top plate is to the right. This has two perpendicular end pieces with screw holes. A reinforcing wall connects these end pieces and runs along the posterior edge of the top plate. The bottom plate is shown attached to a support apparatus. A reinforcing piece can be seen running along the anterior endwall in front of the open region marked with a grid. This is raised sufficiently above the plane of the plate to allow the anterior edge of the top plate to slide underneath. Screw holes can be seen in the endwall running along the sides of the bottom plate. During imaging, the top plate is positioned on top of the bottom plate so that: a) its raised region is nested inside the corresponding open region of the bottom plate; b) its anterior edge is under the reinforcing piece on the anterior endwall of the bottom plate; and c) screws may be inserted through the holes in the endwall on the sides of the bottom plate and into corresponding holes in the perpendicular end pieces of the top plate. After imaging is complete and prior to needle biopsy, the screws between the plates would be removed. The bottom plate would be left in place and the top plate would then be lifted out.

FIG. 7 shows a breast compression apparatus in use during a breast examination. A compression plate is shown above the patient's breasts attached to a support arm.

REFERENCED NUMERALS IN FIGURES

Figure 1:
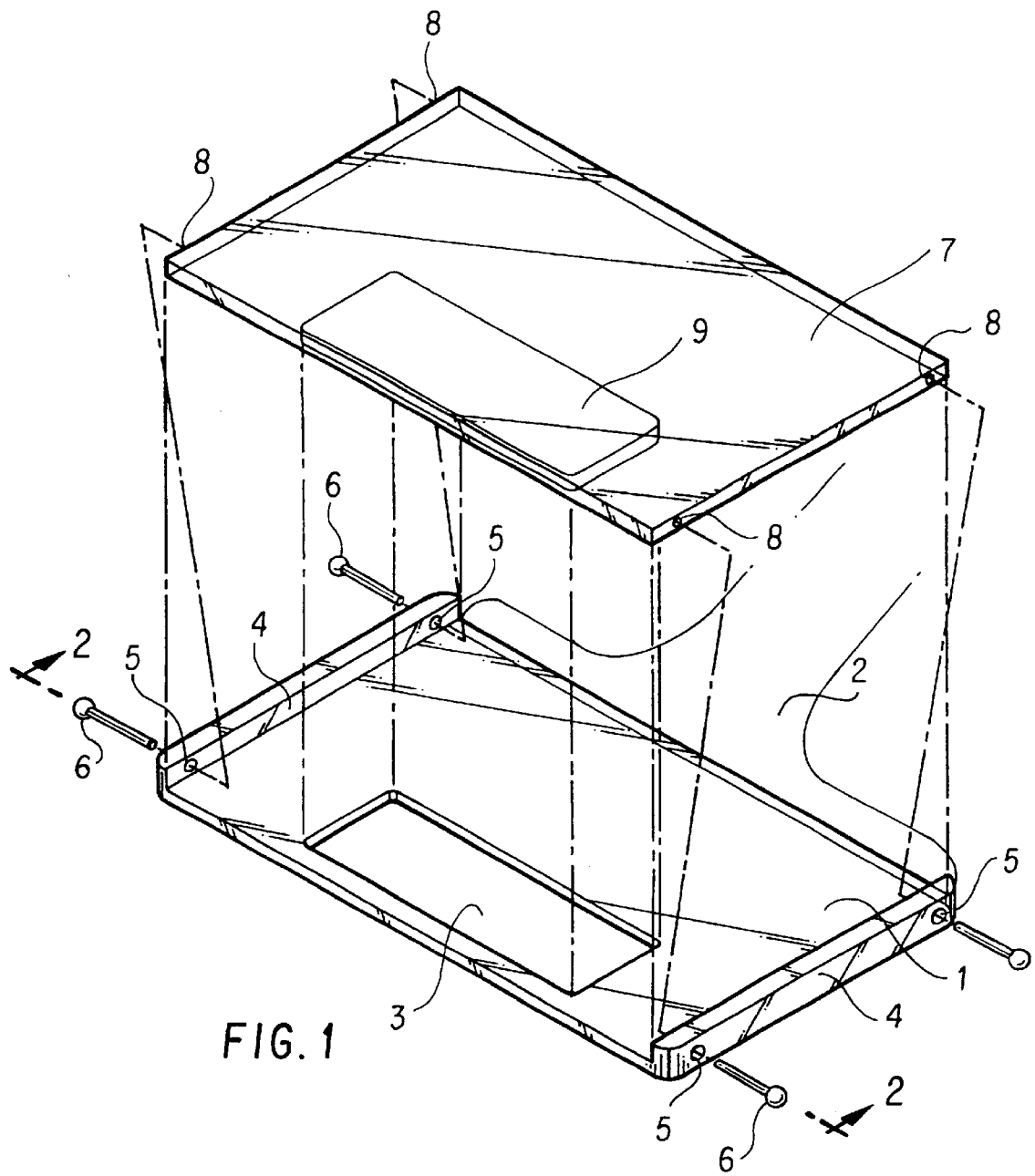
FIG. 1.

In FIGS. 1–7, the following reference numerals are used:
1: bottom plate of compression apparatus
2: support arm(s) attached to compression plate
3: open region, or "window," in bottom compression plate
4: substantially perpendicular end pieces on bottom compression plate
5: screw holes in perpendicular end pieces
6: screws for holding top and bottom compression plates together
7: planar top compression plate
8: screw holes in top compression plate
9: raised element in top compression plate
10: top compression plate (alternative design to (7))
11: perpendicular end pieces on top compression plate
12: screw holes in end pieces of top compression plate
13: screws inserted in holes of top compression plate
14: raised element of top compression plate
15: grid along edges of open region in bottom compression plate
16: reinforcing wall permanently attached to posterior aspect of top compression plate and perpendicular to the plane of the plate
17: reinforcing piece attached to anterior endwall of bottom compression plate and extending (typically about 5 mm) over the plane of the plate. The piece is raised sufficiently above the plane of the bottom plate to form a lip under which the anterior edge of the top plate may be slid. This helps to hold the top plate in place during breast compression for imaging. After imaging, the top plate may be lifted out from this lip and removed.
18: perpendicular endwall running along the sides and anterior edge of the bottom compression plate
19: screw holes in endwall of bottom compression plate

DETAILED DESCRIPTION OF THE INVENTION

The present invention is directed to an apparatus that can be used in procedures for diagnosing breast cancer. The general features of the apparatus are shown in FIG. 1. The apparatus has a bottom compression plate (1) with a smaller internal open region (3). Typically, this plate will be joined to a support arm (2) that can be moved to position the plate against a woman's breast. The exact dimensions of the plate are not critical to the invention, but typically should be about 23 cm lengthwise by about 15 cm on the side. The internal open region should typically be about 1–6 cm on one side by 4–12 cm on the other, with a preferred size being about 4 cm by 8 cm. The plate may be made out of any sturdy rigid material that is X-ray transmissive, e.g., Plexiglass™ or acrylic, and should preferably be optically transparent.

The apparatus will also have a top compression plate (7) with a raised element (9) that corresponds geometrically to the opening in the bottom plate. Thus, when the two plates are joined together, the raised element in the top plate should fit snugly within the open region of the bottom plate to form a flat lower surface for contacting breast tissue. The dimensions of the raised element should be slightly smaller than the open region of the bottom plate so that it fits inside without there being a gap of more than about 0.2 cm. Thus, if the opening in the bottom plate were 4 cm by 8 cm, the raised region of the top plate would typically be about 3.9 cm by 7.9 cm. The raised element should be elevated from the planar surface sufficiently so that when the plates are brought together the lower surface of the bottom plate is substantially flat. Thus, if the bottom plate were 3 cm thick, the raised region of the top plate should be elevated 3 cm above the planar surface. It will usually be made of the same material as the bottom plate. The thickness of both the top and bottom plates, apart from the raised region, will usually be between about 2 and 6 mm with a thickness of about 3 mm being typical.

FIG. 1 shows the bottom plate (1) with two opposing end pieces (4) that are substantially perpendicular and which oppose one another. These end pieces will typically be molded as part of the bottom plate. However, it is also possible that they may be separately molded and then later attached to the bottom plate, e.g., by glue. The end pieces as shown, contain holes (5) which correspond to holes located in the top plate (8). After plates are brought together, screws (6) may be inserted in order to hold the two plates securely together. Any type of screw may be used for this purpose with the sole requirement being that plates be held together sufficiently so that they do not separate during breast compression. Standard procedures may be used for molding and assembling the compression apparatus and alternative means may be employed for holding the plates together. For example, instead of screws, the two plates could simply be joined together with C type clamps or some similar device.

Figure 2:
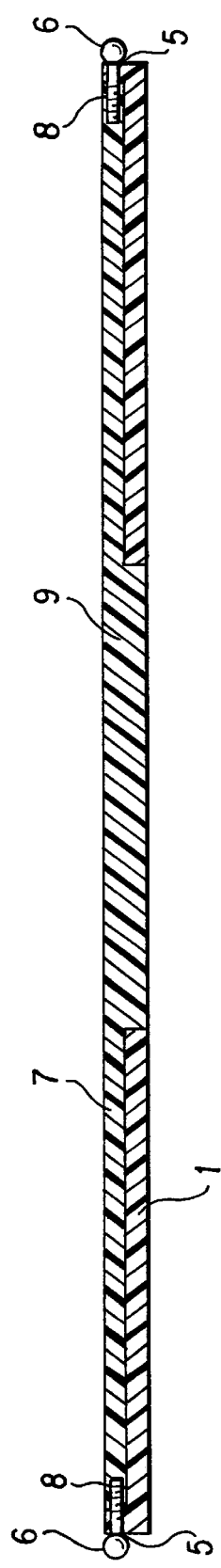
FIG. 2.

A cutaway front view of the two plates joined together is shown in FIG. 2. The holes (8) in the top plate (7) have been aligned with the holes (5) in the bottom plate (1) and screws (6) have been inserted. The raised element of the top plate (9) has filled in the opening in the bottom plate (1) so that a flat bottom surface has been formed.

Figure 3:
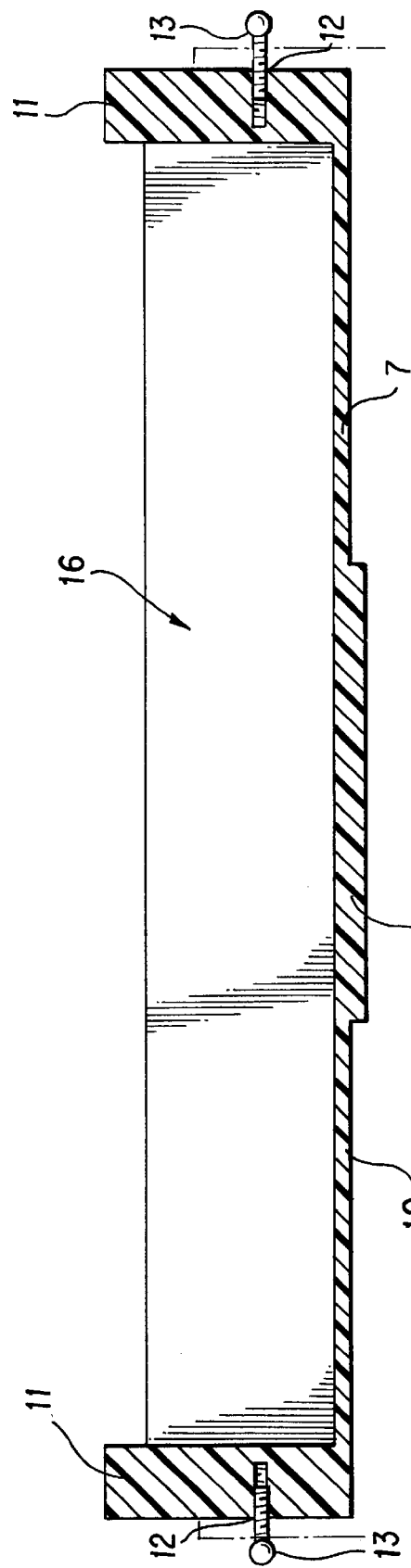
FIG. 3.
Figure 6:
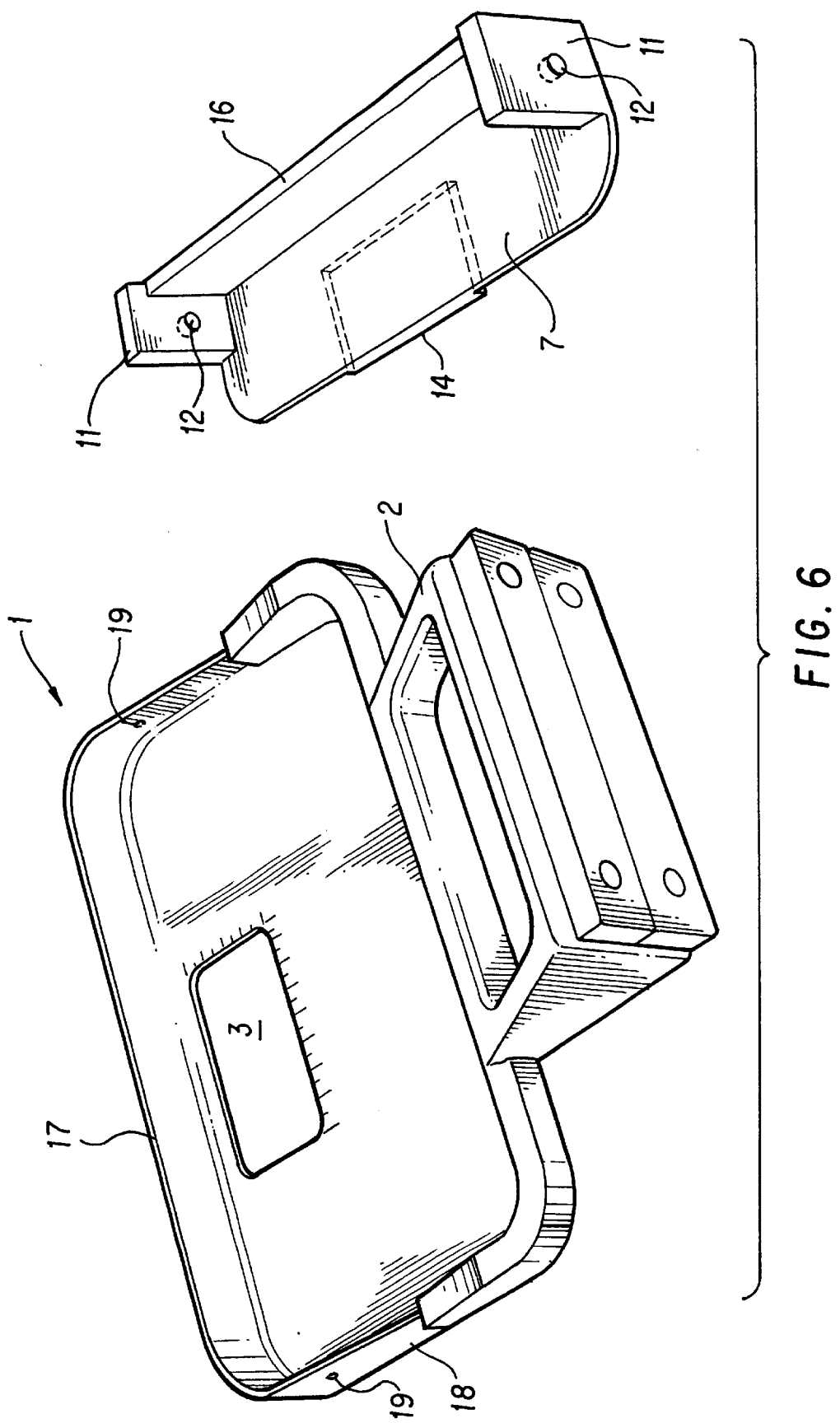
FIG. 6.
Figure 7:
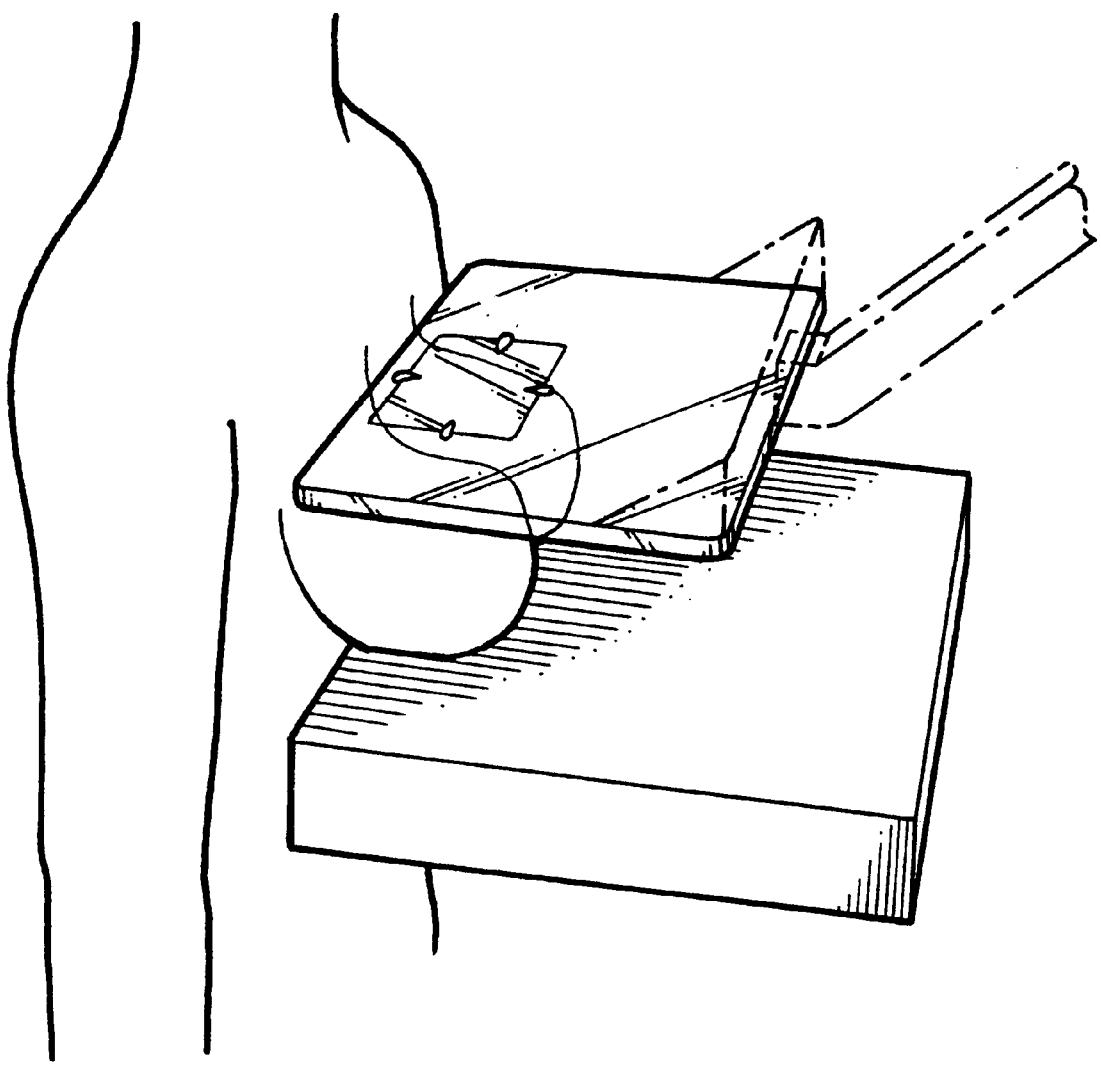
FIG. 7.

An alternative, and preferred, design for a top plate is shown in FIG. 3 (also shown in FIG. 6). In this case, the top plate (10) contains substantially perpendicular end pieces (11) with holes (12) for the insertion of screws (13). There is a reinforcing wall (16) that connects to the end pieces and which is perpendicular to the plane of the top plate. In this design, the bottom plate would generally have a raised endwall with corresponding holes for screw insertion. Thus, screws would be inserted through the holes in the raised endwall of the bottom plate and into the corresponding holes in the end pieces of the top plate to hold the plates together during breast compression. The raised portion of the top plate (14) would be nested inside the corresponding open region of the bottom plate during this procedure.

Figure 4:
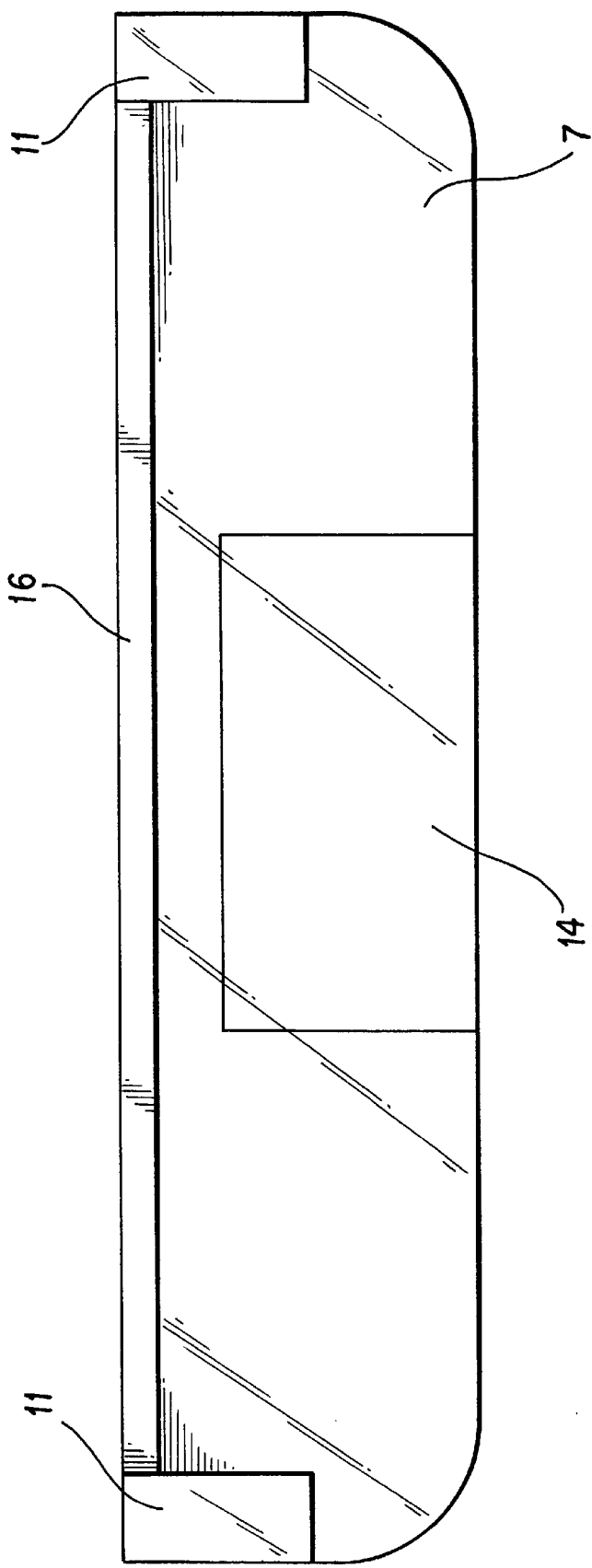
FIG. 4.

The design of the top plate of FIG. 3 is shown viewed from above in FIG. 4. The plane of the plate (7) extends away from the perpendicular reinforcing wall and has the raised region (14) along its anterior edge, i.e. the edge closest to the chest of a subject during imaging. The perpendicular end pieces of the top plate (11) need not extend all the way from the posterior to the anterior edge of the plate. In the design shown, the end pieces extend about half way.

Figure 5:
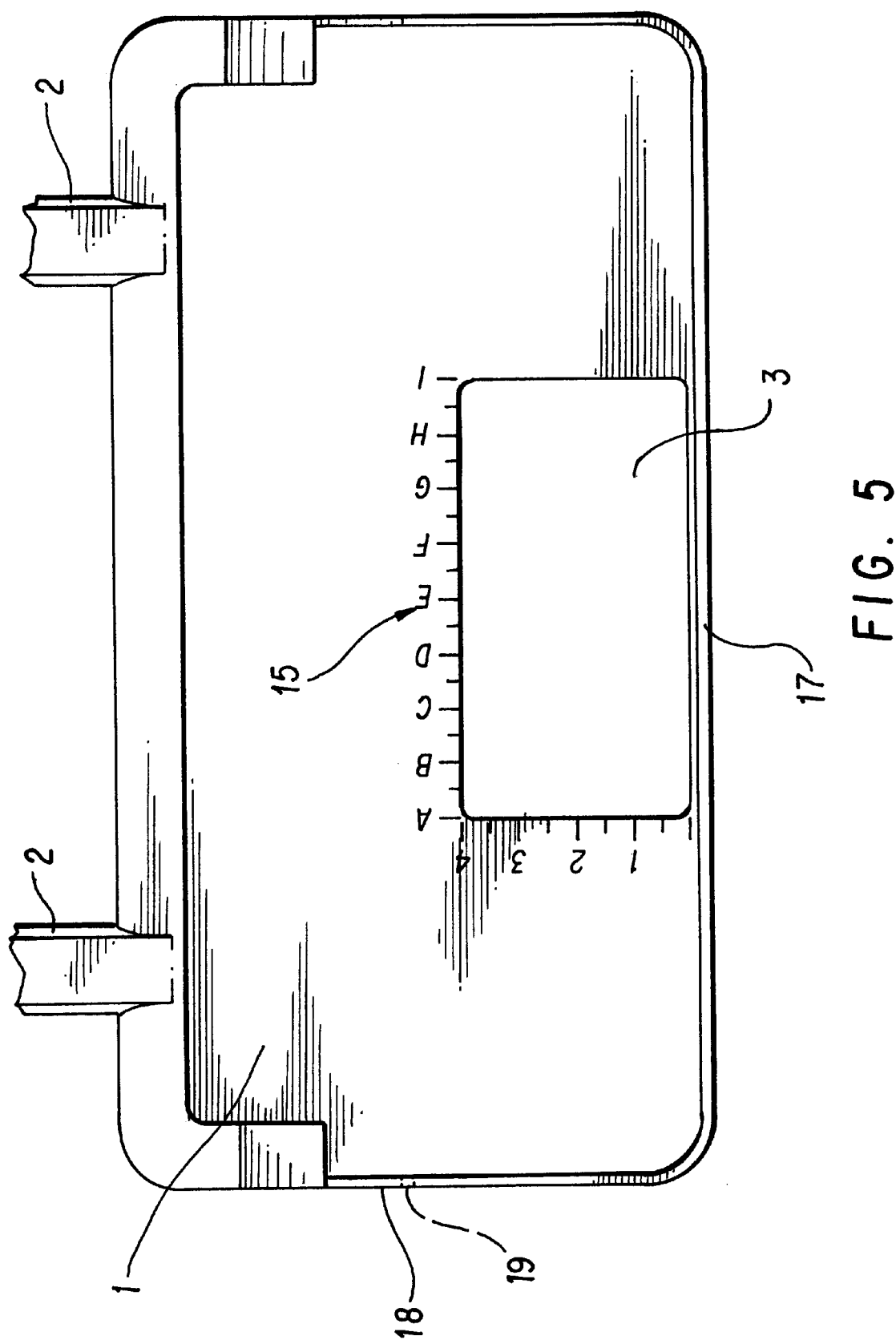
FIG. 5.

A top view of a bottom compression plate (1) is shown in FIG. 5 (also shown in FIG. 6). The open region (3) is shown with a grid (15) running along two of its edges. This is present to aid a physician in needle placement during breast biopsy. Two attachment elements (2) are shown joined to the bottom plate. These would be attached to a support arm used for positioning the plate against breast tissue. The plate contains a perpendicular endwall (18) that runs along the sides and the anterior edge of the plate. Screw holes (19) that can be aligned with screw holes in the end pieces of the top compression plate are in the endwall on either side of the plate. The endwall running along the anterior edge of the plate has an attached reinforcing piece (17). This reinforcing piece extends slightly (about 5 mm) over the plane of the plate and is raised sufficiently above the plate to allow the anterior edge of the top plate to slide under it and make contact. Thus, the reinforcing piece forms a lip on the anterior endwall of the bottom plate that, together with the screws between the top and bottom plates discussed above, helps to prevent the upward displacement of the top plate during breast compression.

The apparatus is suitable for use in any of the imaging or diagnostic procedures known in the art which require breast compression. Most typically, the apparatus will be used in needle biopsy procedures. During the first part of the procedure, the top and bottom compression plates will be joined together and the lower surface of the bottom plate will make contact with the breast undergoing examination. Imaging of the breast will then be performed using x-rays in order to localize the lesion suspected of being cancerous. Once imaging has been completed, the top plate of the compression apparatus will be removed without changing the position of the breast so that tissue is accessible through the open region of the bottom plate. Using a grid along the edges of the open region, the physician performing the biopsy will position the needle prior to insertion. Thereafter, the biopsy will follow standard methods well known in the art for removing tissues or fluid for examination by a pathologist. These are, of course, simply guidelines and the specific procedures used will be determined for an individual patient by the attending physician based upon clinical conditions and using methods well known in the art.

The figures and the description above illustrate the presently preferred embodiments of this invention but should not be construed as limiting its scope. As will be readily apparent to one of skill in the art, devices equivalent to those illustrated may be produced which have other shapes and designs, but which have the same essential feature of having a compression plate with a removable element that is positioned over breast tissue. All other embodiments having this feature which do not differ substantially from those described herein are part of the invention.

What is claimed is:

1. An apparatus for compressing breast tissue during a diagnostic imaging technique or needle biopsy, comprising:
   a) a planar bottom plate comprising an open region;
   b) a planar top plate wherein:
      i) said top plate is designed to make contact with and fit over said bottom plate;
      ii) said top plate has a raised element that corresponds to and fits inside said open region of said bottom plate in such a manner that, when the plates make contact, the open region in said bottom plate is filled to form an essentially flat lower surface for contacting said breast tissue;
   c) reversible means for holding said top plate and said bottom plate together with sufficient force to prevent said plates from separating when said apparatus is used to compress said breast tissue during a diagnostic procedure.

2. The apparatus of claim 1, wherein said bottom plate has a grid for aiding in needle placement during the biopsy of breast tissue, said grid lying along the edge of said open region of said bottom plate.

3. The apparatus of claim 1, wherein said bottom plate has a substantially perpendicular end piece along at least two opposing ends, and wherein said top plate, upon contact with said bottom plate, fits inside each end piece.

4. The apparatus of claim 1, wherein said top plate has a substantially perpendicular end piece along at least two opposing ends.

5. The apparatus of either claim 3 or claim 4, wherein said means for holding said top plate and said bottom plate together is by screws.

6. The apparatus of claim 1, wherein said means for holding said top plate and said bottom plate together is by clamps.

7. In a method of compressing breast tissue during needle biopsy, the improvement comprising applying pressure using an apparatus with a removable member, such that:

a) said removable member is in place to form a flat lower surface that contacts said breast tissue during compression; and b) said removable member is removed to form an open region for needle placement during biopsy.

8. The method of claim 7, wherein said apparatus is that of any one of claims 1–4 or 6.

9. An improved method for diagnostically examining breast tissue for a cancerous lesion, comprising:

a) performing an imaging procedure in which breast tissue is compressed with an apparatus having a flat, planar lower surface and wherein said apparatus has a removable member in contact with said breast tissue;

b) removing said removable member from said apparatus to form an opening over said breast tissue; and c) performing a needle biopsy through said opening in said apparatus.

10. The method of claim 9, wherein said apparatus is that of any one of claims 1–4 or 6.

* * * * *